United States Patent [19]

Starrett, Jr. et al.

[11] Patent Number: 5,523,457
[45] Date of Patent: Jun. 4, 1996

[54] RETINOID-LIKE COMPOUNDS

[75] Inventors: John E. Starrett, Jr., Middletown; Muzammil M. Mansuri, Cheshire; David R. Tortolani, Meriden, all of Conn.

[73] Assignee: Bristol-Myers Squibb Company, New York, N.Y.

[21] Appl. No.: 460,019

[22] Filed: Jun. 2, 1995

Related U.S. Application Data

[63] Continuation of Ser. No. 176,760, Jan. 3, 1994, abandoned.

[51] Int. Cl.$^6$ .................. C07C 261/00; C07C 69/76; C07C 229/00
[52] U.S. Cl. ............... 560/24; 560/48; 560/100; 560/57; 562/455; 562/461; 562/467; 562/471; 562/490; 564/169; 564/174; 564/176; 564/180; 568/705; 568/808
[58] Field of Search .............. 560/24, 48, 100, 560/57; 562/455, 461, 467, 471, 490; 564/169, 174, 176, 180; 568/705, 808

[56] References Cited

U.S. PATENT DOCUMENTS 4,876,381  10/1989  Lang et al. .

FOREIGN PATENT DOCUMENTS

| 0199636A1 | 10/1986 | European Pat. Off. . |
| 0337689A1 | 10/1989 | European Pat. Off. . |
| 2164938 | 4/1986 | United Kingdom . |
| WO93/06086 | 4/1993 | WIPO . |
| W /94/05025 | 3/1994 | WIPO . |

OTHER PUBLICATIONS

Hiroyuki Kagechika, et al, "Retinobenzoic Acids. 1. Structure–Activity Relationships of Aromatic Amides with Retinoidal Activity", Journal of Medicinal Chemistry, 31, No. 11, pp. 2182–2192, 1988. (Correction included, Journal of Medicinal Chemistry, 32, No. 12, p. 2583, 1989).

Peter Loeliger, et al, "Arotinoids, a New Class of Highly Active Retinoids", Eur. J. Med. Chem., Chimica Therapeutica, 15, No. 1, pp. 9–15, 1980.

*Primary Examiner*—José G. Dees
*Assistant Examiner*—Joseph M. Conrad, III
*Attorney, Agent, or Firm*—William T. Han

[57] ABSTRACT

This invention relates to a retinoid mpound of formula I

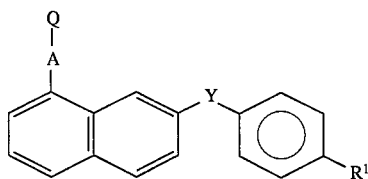

in which
Y is —CO—NH—, —CR$^2$=CR$^3$—, —CO—O—, —O—CO—, —C(=S)—NH—, —C≡C—, —O—CH$_2$—, —CH$_2$—O—, or —CH$_2$—CH$_2$—;
A is —(CH$_2$)$_t$— or a bond;
Q is phenyl optionally substituted with one to three same or different C$_{1-6}$alkyl, C$_{1-6}$alkoxy, halogen, or —CO$_2$R$^4$;
R$^1$ is —CO$_2$Z, —CONHR$^5$, C$_{1-6}$alkyl, —CH$_2$OH, or —CHO;
R$^2$, R$^3$, R$^4$, R$^5$, and Z are independently hydrogen or C$_{1-6}$alkyl;
t is one to six.

18 Claims, 1 Drawing Sheet

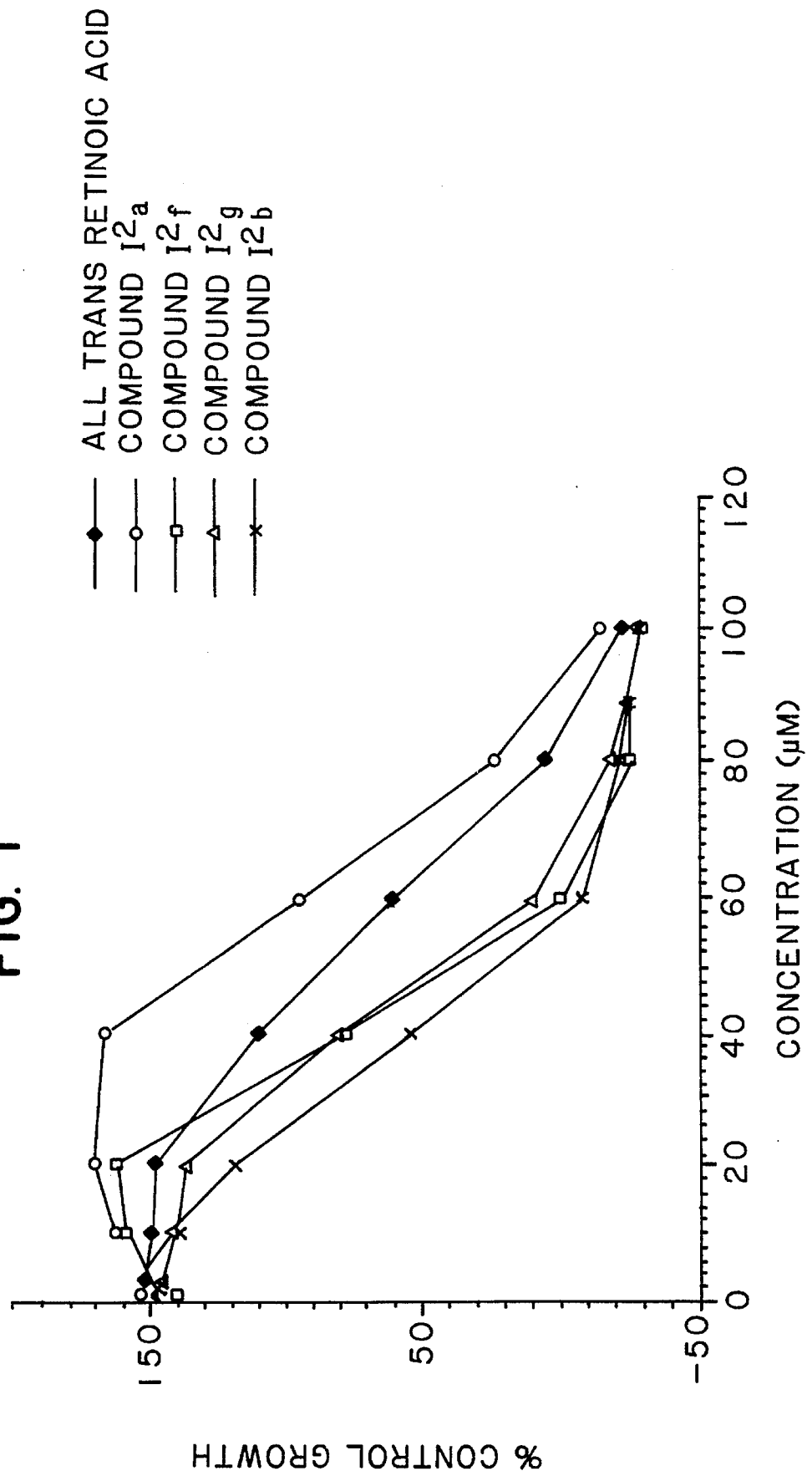

RETINOID-LIKE COMPOUNDS

CROSS-REFERENCE TO RELATED APPLICATION

This application is a continuation of U.S. Ser. No. 08/176,760, filed Jan. 3, 1994 now abandoned.

FIELD OF INVENTION

The present invention provides compounds having retinoid-like activity. More specifically, the compounds of the present invention are useful for preventing and/or treating various skin disorders, such as, but not limited to, acne, psoriasis and damage from irradiation. Further, they have antitumor activities.

BACKGROUND OF THE INVENTION

Retinoic acid and its natural and synthetic analogues (retinoids) exert a wide array of biological effects.

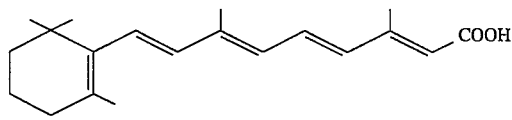

Retinoic Acid

They have been shown to affect cellular growth and differentiation and are promising drugs for the treatment of several cancers. Roberts, A. B. and Sporn, M. B. in "The Retinoids," Sporn, M. B., Roberts, A. B., and Goodman, D. S., eds, 1984, 2 pp. 209–286, Academic Press, New York; Lippman, S. M., Kessler, J. F., and Meyskens, F. L., *Cancer Treat. Rep.*, 1987, 71, p. 391; ibid., p. 493; Hong, W. K. et al., *N. Engl. J. Med.*, 1990, 323, P. 795; Huang, M. et al., *Blood*, 1988, 72, p. 567. A few retinoids are already in clininal use in the treatment of dermatological diseases such as acne and psoriasis. For example, isotretinoin is used clinically for oral therapy of severe acne, and etretinate is particularly useful in the treatment of psoriasis. Orfanos, C. E., Ehlert, R., and Gollnick, H., *Drugs*, 1987, 34, pp. 459–503.

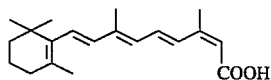

ISOTRETINOIN

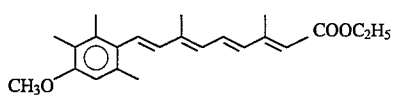

ETRETINATE

Other examples of retinoid compounds include arotinoid of formula II and retinobenzoic acid of formula III, in which X equals —NHCO—, —CONH—, —COCH=CH—, —CH=CHCO—, —COCH$_2$—, etc.

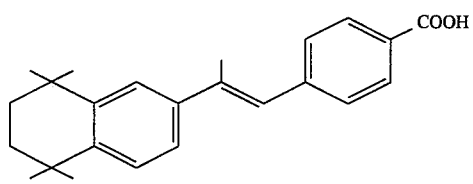

II

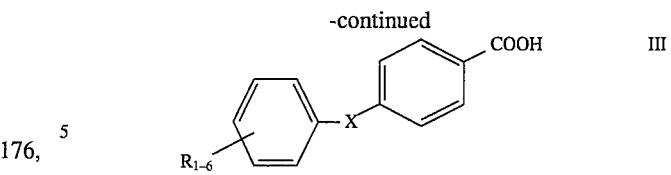

III

See for example: Loeliger, P., Bollag, W., and Mayer, H., *Eur. J. Med. Chem.* 1980, 15, pp 9–15; Kagechika, H. et al., *J. Med. Chem.*, 1988, 31, No. 11, pp 2182–2192.

SUMMARY OF THE INVENTION

This invention relates to a compound of formula I

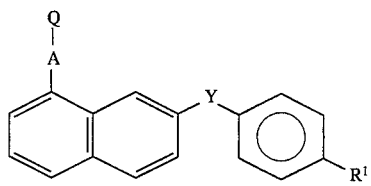

I or a nontoxic pharmaceutically acceptable salt, physiologically hydrolyzable ester or solvate thereof, in which Y is —CO—NH—, —CR$^2$=CR$^3$—, —CO—O—, —O—CO—, —C(=S)—NH—, —C≡C—, —O—CH$_2$—, —CH$_2$—O—, or —CH$_2$—CH$_2$—;

A is —(CH$_2$)$_t$— or a bond;

Q is phenyl optionally substituted with one to three same or different C$_{1-6}$alkyl, C$_{1-6}$alkoxy, halogen, or —CO$_2$R$^4$;

R$^1$ is —CO$_2$Z, —CONHR$^5$, C$_{1-6}$alkyl, —CH$_2$OH, or —CHO;

R$^2$, R$^3$, R$^4$, R$^5$, and Z are independently hydrogen or C$_{1-6}$alkyl;

t is one to six; and with the proviso that —A—Q cannot be

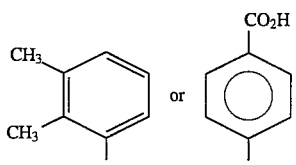

when Y is —CO—NH—.

Also provided by this invention are methods for preventing and/or treating tumors and non-malignant skin disorders comprising administering a compound of formula I to a mammal. Further provided is a pharmaceutical formulation (composition) comprising a compound of formula I in admixture with (a) pharmaceutically acceptable excipient(s).

BRIEF DESCRIPTION OF THE DRAWING

FIG. 1 is the cytotoxicity dose response curves for lung line L2987.

DETAILED DESCRIPTION OF THE INVENTION

This invention relates to a compound of formula I

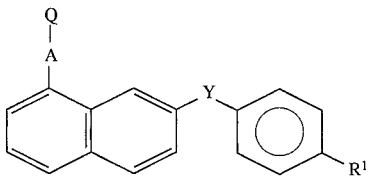

or a nontoxic pharmaceutically acceptable salt, physiologically hydrolyzable ester or solvate thereof,
in which Y is —CO—NH—, —CR$^2$=CR$^3$—, —CO—O—, —O—CO—, —C(=S)—NH—, —C≡C—, —O—CH$_2$—, —CH$_2$—O—, or —CH$_2$—CH$_2$—;

A is —(CH$_2$)$_t$— or a bond;

Q is phenyl optionally substituted with one to three same or different C$_{1-6}$alkyl, C$_{1-6}$alkoxy, halogen, or —CO$_2$R$^4$;

R$^1$ is —CO$_2$Z, —CONHR$^5$, C$_{1-6}$alkyl, —CH$_2$OH, or —CHO;

R$^2$, R$^3$, R$^4$, R$^5$, and Z are independently hydrogen or C$_{1-6}$alkyl;

t is one to six; and with the proviso that —A—Q cannot be

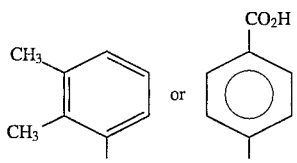

when Y is —CO—NH—.

In the instant application, the numbers in subscript after the symbol "C" define the number of carbon atoms a particular group can contain. For example, C$_{1-6}$alkyl refers to straight and branched chain alkyl groups with one to six carbon atoms and such groups include methyl, ethyl, n-propyl, isopropyl, n-butyl, t-butyl, n-pentyl, n-hexyl, 3-methylpentyl, or the like alkyl groups; C$_{1-6}$alkyloxy (alkoxy) refers to straight or branched alkyloxy groups such as methoxy, ethoxy, n-propoxy, i-propoxy, n-butoxy, t-butoxy (t-butyloxy), n-pentyloxy, n-hexyloxy, or 3-methylpentyloxy, to name a few; aryl refers to phenyl optionally substituted with one to three same or different C$_{1-6}$alkyl, C$_{1-6}$alkoxy, halogen, or —CO$_2$R$^4$; and halogen refers to fluorine, chlorine, bromine, or iodine. In the instant application all symbols once defined retain the same meaning until they are redefined.

Some compounds of formula I may also form pharmaceutically acceptable metal and amine salts in which the cation does not contribute significantly to the toxicity or biological activity of the salt. These salts are also part of the present invention. Suitable metal salts include the sodium, potassium, calcium, barium, zinc, and aluminum salts. The sodium or potassium salts are preferred. Amines which are capable of forming stable salts group include trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine, or the like pharmaceutically acceptable amines.

When compounds of formula I contains carboxy groups, it can form physiologically hydrolyzable esters which serve as prodrugs by being hydrolyzed in the body to yield the retinoids per se. They are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include C$_{1-6}$alkyl, benzyl, 4-methoxybenzyl, indanyl, phthalidyl, methoxymethyl, C$_{1-6}$alkanoyloxyC$_{1-6}$alkyl, e.g. acetoxymethyl, pivaloyloxymethyl or propionyloxymethyl, C$_{1-6}$alkoxycarbonyloxyC$_{1-6}$alkyl, e.g. methoxycarbonyloxymethyl or ethoxycarbonyloxymethyl, glycyloxymethyl, phenylglycyloxymethyl, (5-methyl-2-oxo-1-3-dioxolen-4-yl)methyl and other well-known physiologically hydrolyzable esters used, for example, in the penicillin and cephalosporin arts. Such esters are prepared by conventional techniques know in the art.

The structural formulae as drawn in the instant application are believed to best represent the structures of compounds of the present invention. However, some compounds within the scope of the invention may exist as other tautomeric forms, in which hydrogen atoms are transposed to other parts of the molecules and the chemical bonds between the atoms of the molecules are consequently rearranged. It should be understood that the structural formulae represent all tautomeric forms, insofar as they may exist.

The synthesis of a compound of formula I can be accomplished by a wide variety of methods using conventional starting materials and processes. The synthetic descriptions and specific examples that follow are only intended for the purpose of illustration, and are not to be construed as limiting in any manner ways to make compounds of the present invention by other methods.

Typically a compound of formula I may be made by employing one of the processes or an obvious variation thereof as described in Schemes II to VI. The processess of Scheme II to IV employ a compound of formula X, in which R$^{11}$ is C$_{1-6}$alkyl, preferably methyl or ethyl. A compound of formula X can in turn be made by a process of Scheme I.

In Scheme II, an aryl bromide of formula XI is subjected to a halogen-metal exchange with an C$_{1-6}$alkyllithium. Subsequently, the resultant aryllithium is coupled with a compound of formula X in the presence of ZnCl$_2$ and [1,3-bis(diphenylphosphino)propane]nickel (II) chloride (Ni dpppCl$_2$) to afford a compound of formula I$^1$, a compound within the scope of formula I compounds. The preferred C$_{1-6}$alkyllithium for the halogen-metal exchange is t-butyllithium. As used herein, R$^a$, R$^b$, and R$^c$ are independently hydrogen, C$_{1-6}$alkyl, C$_{1-6}$alkoxy, halogen, or —CO$_2$R$^4$. In a compound of formula XI, R$^a$, R$^b$, and R$^c$ are preferably hydrogen, C$_{1-6}$alkyl or fluoro. If desired, the ester group in a compound of formula I$^1$ may be hydrolyzed to afford an acid of formula I$^2$.

Alternatively, a compound of formula X may be coupled with an aryl stananne of formula XV in the presence of bis(triphenylphosphine) palladium (II) chloride and lithium chloride to afford a compound of formula I$^3$. In a compound of formula XV, R$^a$, R$^b$, and R$^c$ are preferably hydrogen, C$_{1-6}$alkyl, halogen or C$_{1-6}$alkylester. If desired, ester group(s) in a compound of formula I$^3$ may be converted to carboxy group(s) by hydrolysis to afford a compound of formula I$^4$. Scheme III.

In another embodiment, an arylalkyl Grignard of formula XII may be coupled, in the presence of zinc chloride and Ni dpppCl$_2$ with a compound of formula X to afford a compound of formula I$^5$. Hydrolysis of ester group(s) affords a compound of formula I$^6$. Scheme IV.

As shown in Scheme V, a series naphthyl-2-ketone derivatives of formula XIV can be made by reacting $R^{12}Li$, in which $R^{12}$ is $C_{1-6}$alkyl, preferably a straight chain $C_{1-6}$alkyl, with naphthyl-2-carboxylic acid of formula XIII. Subsequently, an anion of p-[ (diethoxyphosphoryl)methyl]benzene derivative of formula XVI can be reacted with a compound XIV in a routine Horner-Emmons Wadsworth-Emmons reaction (see: *Org. React.*, 25, 73–253 (1977); Stec, *Acc. Chem. Res.*, 411–417 (1983)) to afford additional compounds within formula I. As used herein, $R^{13}$ is hydrogen or $C_{1-6}$alkyl. Further hydrolysis of ester group(s) affords a compound of formula $I^8$.

Some other compounds within the scope of formula I can be made by methods comprising Processes A–H of Scheme VI or variations thereof. All starting materials are conventional materials which are either commercially available or can be readily made by a person skilled in the art. Processes A–H are also conventional organic transformations well known in the art. For example, Process E can be achieved through palladium mediated Heck Reaction described by Richard Heck in "Palladium Reagents in Organic Synthesis" Academic Press, New York (1985). The conversion of Process C can be achieved by $P_2S_5$ described by R. T. Dean and H. Rapoport in the *Journal of Organic Chemistry*, 43, 2116 (1978). The reduction of the triple bond in Process D can be accomplished via $Na/NH_3$ described by W. Boland et al. in *Synthesis*, p 114 (1979).

Scheme I

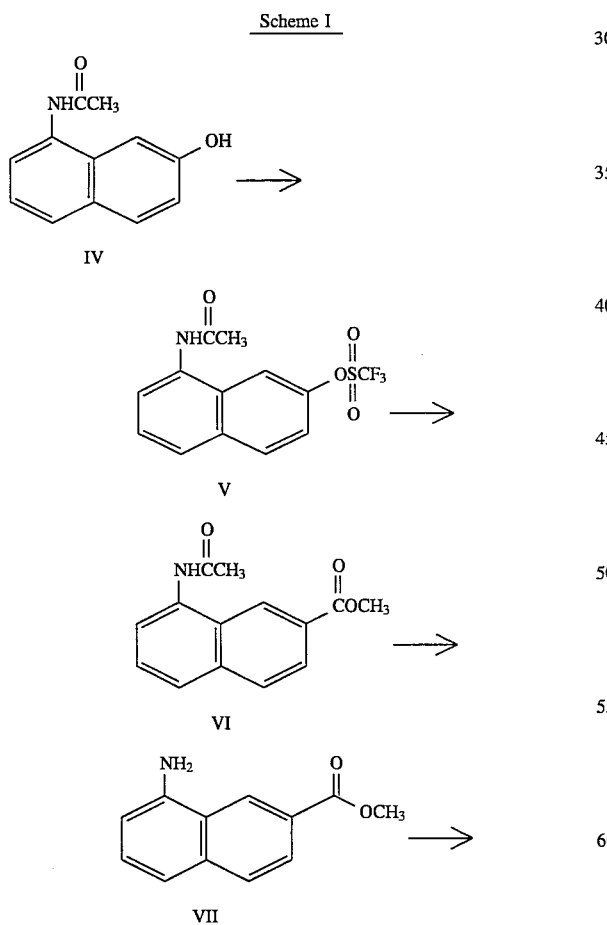

Scheme I -continued

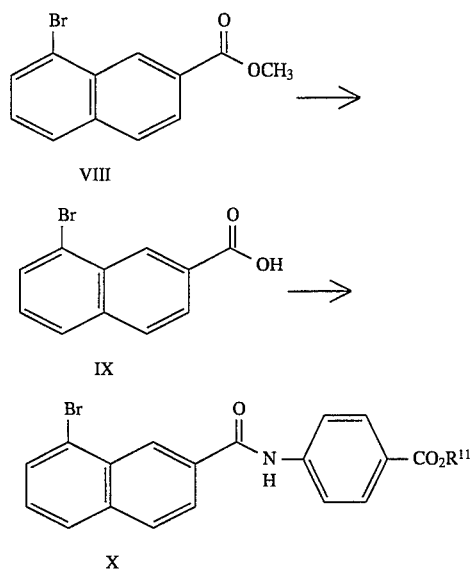

Scheme II

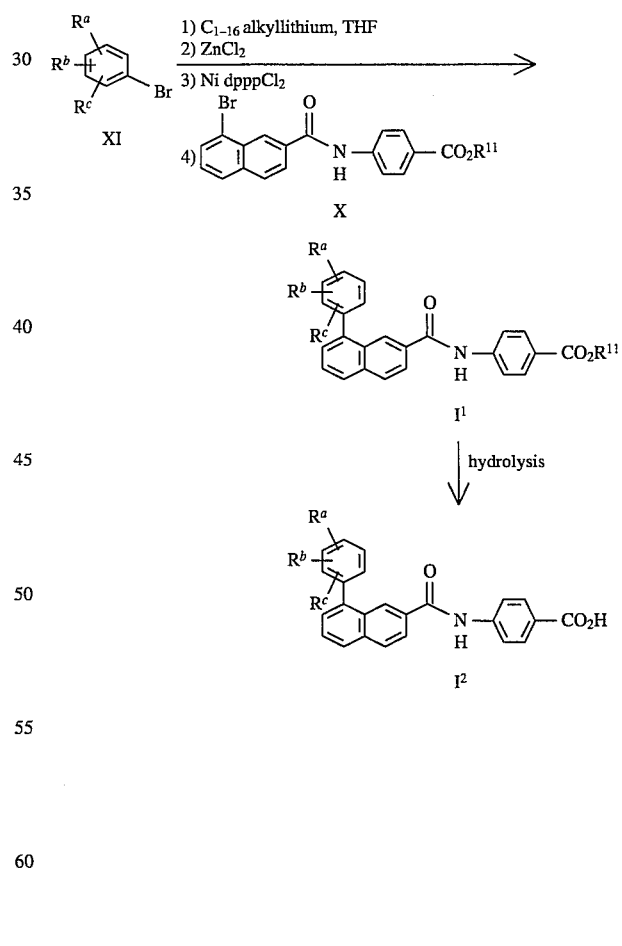

Scheme III
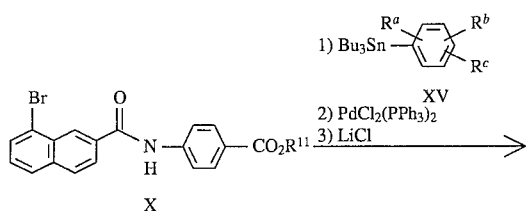
Scheme IV
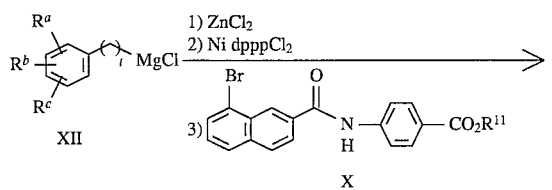
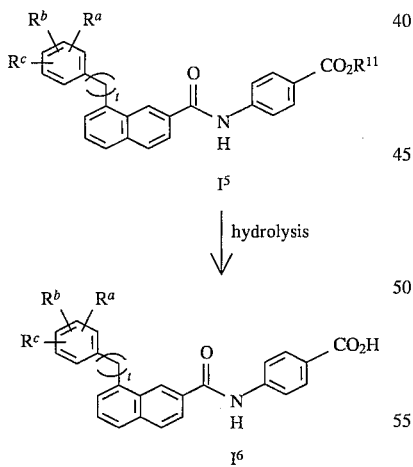
Scheme V
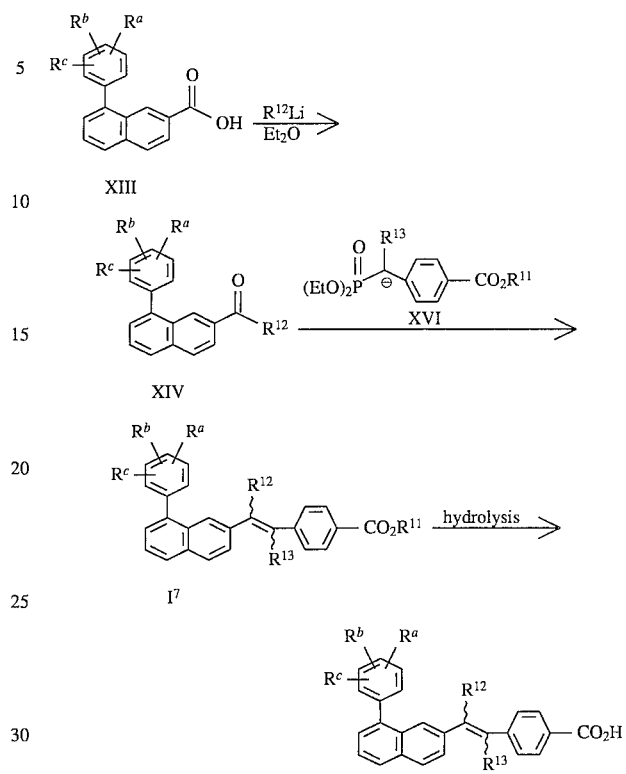

SCHEME VI

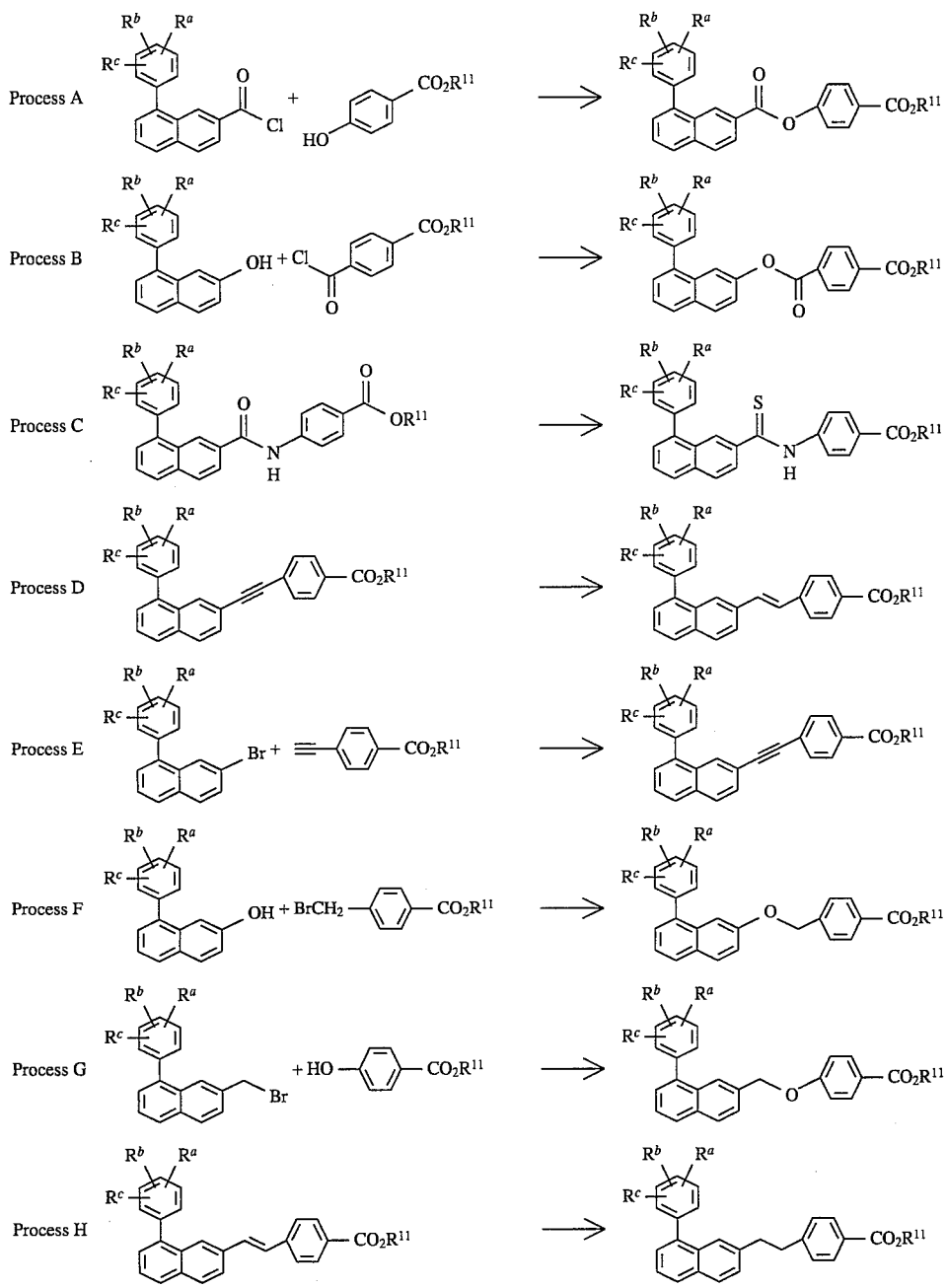

DESCRIPTION OF SPECIFIC EMBODIMENTS

The specific examples which follow illustrate the synthesis of representative compounds of the instant invention and are not to be construed as limiting the invention in sphere or scope. The methods may be adapted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiplet (m), doublet (d), quartet (q), triplet (t), doublet of doublet (dd), doublet of triplet (dt), and doublet of quartet (dq). The solvents employed for taking NMR spectra are DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value.

Celite is a registered trademark of the Johns-Manville Products Corporation for diatomaceous earth.

The abbreviations used herein are conventional abbreviations widely employed in the art. Some of which are:

| MS | mass spectrometry |
|---|---|
| HRMS | high resolution mass spectrometry |
| Ph | phenyl |
| Ar | aryl |
| DCI | desorption chemical ionization |
| Hex | hexane(s) |
| tBu | tertiarybutyl |

EXAMPLE 1

2-Trifluoromethanesulfonyloxy-8-acetylaminonaphthalene (V)

To a stirred solution of 10.0 g (49.7 mmol) of 1-acetylamino- 7-naphthol (IV) (purchased from Pfaltz & Bauer) and 16.80 g (137.5 mmol) of 4-dimethylaminopyridine in 400 mL of anhydrous $CH_2Cl_2$ was added 7.50 mL (44.6 mmol) of trifluoromethanesulfonic anhydride dropwise at 0° C. After stirring at 0° C. for 1 hour, an additional 2.40 g (19.6 mmol) of 4-dimethylaminopyridine and 0.75 mL (4.5 mmol) of trifluoromethane anhydride were added. After 1 hour, the mixture was washed twice with 1N HCl (400 mL) and once with $H_2O$(400 mL). The organic layer was then separated and concentrated in vacuo. The residue was purified by silica gel chromatography, eluting with 5% EtOAc/Hex to give 11.50 g (yield: 69.5%) of the title compound; $^1$H-NMR: δ7.90 (d, J=8.9 Hz, 1H), 7.78 (d, J=7.3 Hz, 1H), 7.71 (s, 1H), 7.50 (m, 2H), 7.35 (d, J=8.8 Hz, 1H), 2.30 (s, 3H); MS(DCI) m/e: 334 (MH$^+$).

EXAMPLE 2

8-Acetylamino-2-naphthoic acid, methyl ester (VI)

To a stirred solution of 2-trifluoromethanesulfonyloxy-8-acetylaminonaphthalene (V) (11.5 g, 34.5 mmol) in 100 mL of methanol and 100 mL of dimethyl sulfoxide was added 10.50 mL (75.65 mmol) of triethylamine, 229 mg (1.00 mmol) of palladium (II) acetate and 425 mg (1.00 mmol) of 1,3-bis(diphenylphosphino)propane. The reaction mixture was then saturated with carbon monoxide and heated to 70° C. under a balloon of carbon monoxide for 2 hours. At this time, the mixture was cooled to room temperature, poured into water and extracted with ethyl acetate. The organic layer was then separated, dried over anhydrous magnesium sulfate and concentrated in vacuo to give 8.20 g (yield: 98.5%) of the title compound; $^1$H-NMR: 8.61 (s, 1H), δ8.02 (m, 2H), 7.86 (m, 1H), 7.68 (m, 2H), 7.55 (m, 1H), 3.97 (s, 3H), 2.34 (s, 3H); MS(DCI) m/e: 242 (MH$^+$).

EXAMPLE 3

8-Amino-2-naphthoic acid, methyl ester (VII)

A stirred solution of 8.0 g (33 mmoles) of 8-acetylamino-2-naphthoic acid, methyl ester (VI) in 50 mL of methanol and 35 mL of 12N HCl was allowed to reflux for 1.5 hours. The reaction mixture was then cooled to 0° C., and pH adjusted to 6.5 with 10N NaOH. Removal of methanol in vacuo followed by collection of precipitate by vacuum filtration followed by washing with $H_2O$ and air drying afforded 5.72 g (yield: 80%) of 8-amino-2-naphthoic acid, methyl ester; $^1$H-NMR: δ8.62 (s, 1H), 7.99 (dd, J=8.5 Hz, 1.4 Hz, 1H), 7.78 (d, J=8.5 Hz, 1H), 7.36 (m, 1H), 7.25 (d, J=8.4 Hz, 1H), 6.79 (d, J=7.1 Hz, 1H), 4.35 (bs, 2H), 3.95 (s, 3H); MS (DCI) m/e: 218 (MH$^+$).

EXAMPLE 4

8-Bromo-2-naphthoic acid, methyl ester (VIII)

To a cooled (10° C.) stirred solution of $NaNO_2$ (2.18 g, 31.5 mmol) in concentrated $H_2SO_4$ (28.3 mL) and glacial acetic acid (26.1 mL) (prepared by adding $NaNO_2$ to cooled [10° C.] $H_2SO_4$, heating to dissolve, re-cooling and adding HOAc) was added a solution of 8-amino-2-naphthoic, methyl ester (VII) (5.72 g, 26.36 mmoles) in glacial acetic acid (88.7 mL) over 10 minutes. The resulting solution was then added slowly (over 10 minutes) to a heated (60° C.), stirred solution of CuBr (16.59 g, 43.31 mmoles) in concentrated HBr (160 mL). The mixture was warmed to 90° C. for 10 minutes, cooled, diluted with $H_2O$ (350 mL), and filtered to give 5.8 g (yield: 83%) of 8-bromo-2-naphthoic acid, methyl ester; $^1$H-NMR: δ9.00 (s, 1H), 8.10 (dd, J=7.5, 1.0 Hz, 1H), 7.90 (d, J=8.5 Hz, 1H), 7.85 (d, J=6.5 Hz, 2H), 7.40 (dd, J=8.2, 7.5 Hz, 1H), 4.05 (s, 3H).

EXAMPLE 5

8-Bromo-2-naphthoic acid (IX)

To a stirred solution of 5.73 (21.6 mmoles) of 8-bromo-2-naphthoic acid, methyl ester (VIII) in 50.0 mL of ethanol was added 21.6 mL (216 mmoles) of 10N NaOH at room temperature. After 1 hour, an excess of 1N HCl was added. The precipitate was collected, washed with 1N HCl and air dried to give 5.40 g (yield: 99%) of 8-bromo- 2-naphthoic acid; $^1$H-NMR: δ13.35 (bs, 1H), 8.80, (s, 1H), 8.11 (m, 3H), 7.98 (d, J=8.0 Hz, 1H), 7.59 (dd, J=7.2 Hz, 1H).

EXAMPLE 6

4-[[(8-Bromo-2-naphthalenyl)carbonyl]amino]benzoic acid, ethyl ester (Xa)

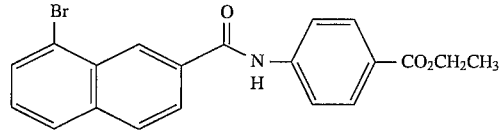

A solution of 8-bromo-2-naphthoic acid (IX) (524 mg, 2.09 mmoles) in 15 mL of $SOCl_2$ with two drops of dimethylformamide was allowed to stir at room temperature. The mixture became homogeneous within 30 minutes and was then concentrated in vacuo. The residue was then taken up in 15 mL of anhydrous pyridine and treated with (2.30 mmoles) of p-aminobenzoic acid, ethyl ester. After 4 hours, 1N HCl was added to the mixture. The resulting mixture was extracted with ethyl acetate, washed with 1N HCl (200 mL×4) and washed with saturated sodium bicarbonate (200 mL×2). The organic phase was then separated, dried over magnesium sulfate and concentrated in vacuo to give 751 mg (yield: 90%) of the title compound;

$^1$H-NMR(CDCl$_3$): δ8.79 (s, 1H), 8.15 (bs, 1H), 8.08 (d, 8.75 Hz, 2H), 7.95 (m, 2H), 7.87 (d, J=7.6 Hz, 2H), 7.78 (d, J=8.75 Hz, 2H), 7.42 (m, 1H), 4.35 (q, J=7.5 Hz, 2H), 1.40 (t, J=7.5 Hz, 3H).

(DCI) m/e: 398(MH$^+$)—based on bromine 79.

Different alkyl esters of a compound Xa can be made analogously.

EXAMPLE 7

4-[[(8-Aryl-2-naphthlenyl)carbonyl]amino]benzoic acid (I$^2$)

(Step 1: To a solution of an aryl bromide of formula XI (6.31 mmol) in tetrahydrofuran (10.0 mL) at 78° C. is added t-butyllithium (1.7M solution in hexane, 8.17 mL, 13.96 mmol). The mixture is stirred at −78° C. for 15 minutes and then a 1M zinc chloride solution in ether (6.31 mL, 6.31 mmol) is added. After 1 hour at room temperature, [1,3-bis(diphenylphosphino)propane]nickel (II) chloride (68 mg, 0.126 mmol) and 4-[[(8-bromo- 2-naphthalenyl)carbonyl]amino]benzoic acid, alkyl ester (X)(1.26 mmol) are added and the mixture is stirred at room temperature between 3 and 72 hours. The mixture is diluted with water (100 mL) and extracted with ethyl acetate (100 mL×2). The combined organic phase is evaporated and the residue is chromatographed on silica gel (eluted with 20% ethyl acetate in hexane) to give the appropriate 4-[[(8-aryl-2-naphthlenyl)carbonyl]amino]benzoic acid, alkyl ester ($I^1$).

Step 2: To a solution of a compound of formula $I^1$ (0.62 mmol) in ethanol (10 mL) at room temperature is added a 10N NaOH solution (0.62 mL, 6.2 mmol). After 48 hours, the mixture is diluted with an excess of 1N HCl (100 mL) and then filtered, washed with water and dried to provide a benzoic acid of formula $I^2$.

EXAMPLE 8

The following compounds of formula $I^{2'}$ were made by the general two-step process of Example 7. The yield refers to the overall yield of Step 1 and Step 2.

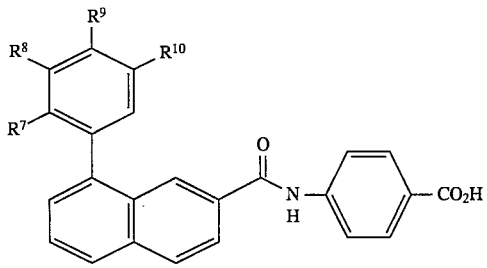

4-[[(8-phenyl-2-naphthalenyl)carbonyl]amino]benzoic acid ($I^2$a) ($R^7, R^8, R^9, R^{10}$=H)
$^1$H-NMR: δ12.76 (bs, 1H), 10.65 (bs, 1H), 8.44 (s, 1H), 8.16 (d, J=8.6 Hz, 1H), 8.07 (m, 2H), 7.86–7.96 (m, 4H), 7.70 (m, 1H), 7.46–7.58 (m, 6H); m.p. 277°–280° C.; IR (KBr): 3448, 1686, 1518; $^{13}$C-NMR: 166.97, 166.19, 143.28, 140.76, 139.51, 134.90, 132.42, 130.25, 130.00, 129.93, 128.66, 127.96, 127.76, 127.57, 126.35, 125.60, 124.18, 119.61; MS (DCI) m/e: 368 (MH$^+$).
Anal. calcd. for $C_{24}H_{17}O_3N_1$.0.18 $H_2O$: C, 77.77; H, 4.72; N, 3.78. Found: C, 77.77; H, 4.37; N, 4.07.
4-[[[8(3,5-Dimethylphenyl)-2-naphthalenyl]carbonyl]amino]benzoic acid ($I^2$b) ($R^7, R^9$=hyrdrogen; $R^8, R^{10}$=CH$_3$)
Yield: 68%; $^1$H-NMR: δ12.78 (bs, 1H), 10.67 (bs, 1H), 8.43 (s, 1H), 8.15 (d, J=8.6 Hz, 1H), 8.06 (m, 2H), 7.92 (m, 4H), 7.69 (m, 1H), 7.50 (dd, J=6.9 Hz, 0.6Hz, 1H), 7.14 (s, 2H), 7.11 (s, 1H), 2.36 (s, 6H); $^{13}$C-NMR: 168.66, 167.97, 145.01, 142.76, 141.185, 139.32, 136.55, 134.04, 131.96, 130.84, 130.29, 129.41, 129.36, 129.20, 129.06, 128.23, 127.29, 125.80, 121.26, 22.69; MS (DCI) m/e: 396 (MH$^+$); IR (KBr): 3442, 1684, 1594, 1518.
Anal. calcd. for $C_{26}H_{21}O_3N_1$: C, 78.96; H, 5.35; N, 3.54. Found: C, 78.55; H, 5.25; N, 3.28.
4-[[[8-(3-Methylphenyl)-2-naphthalenyl]carbonyl]amino]benzoic acid ($I^2$c) ($R^7, R^9, R^{10}$=hydrogen; $R^8$=CH$_3$)
$^1$H-NMR: δ12.78 (bs, 1H), 10.68 (bs, 1H), 8.45 (s, 1H), 8.16 (d, J=8.6 Hz, 1H), 8.08 (m, 2H), 7.92 (m, 4H), 7.70 (m, 1H), 7.52 (d, J=6.9 Hz, 1H), 7.44 (m, 1H), 7.34 (m, 3H), 2.42 (s, 3H); $^{13}$C-NMR: 168.67, 167.94, 145.00 142.61, 141.19, 139.60, 136.58, 134.08, 132.17, 131.96, 131.76, 130.32, 130.14, 130.08, 129.53, 129.23, 129.16, 128.77, 128.15, 127.30, 125.86, 121.30, 22.80; MS (DCI) m/e: 382 (MH$^+$); IR (KBr): 3440, 1684, 1518, 1594.
Anal. calcd. for $C_{25}H_{19}O_3N_1$.0.25 $H_2O$: C, 77.81; H, 5.01; N, 3.63. Found: C, 77.71; H, 5.01; N, 3.50.
4-[[[8-(4-Methylphenyl)-2-naphthalenyl]carbonyl]amino]benzoic acid ($I^2$d) ($R^7, R^8, R^{10}$=hydrogen; $R^9$=CH$_3$)
Yield: 40%; $^1$H-NMR: δ12.78 (bs, 1H), 10.66 (bs, 1H), 8.46 (s, 1H), 8.16 (d, J=8.6 Hz, 1H), 8.06 (m, 2H), 7.92 (m, 4H), 7.70 (m, 1H), 7.52 (d, J=7.1 Hz, 1H), 7.40 (m, 4H), 2.41 (s, 3H); $^{13}$C-NMR: 168.66, 167.95, 144.99, 142.47, 138.75, 138.29, 136.63, 134.05, 131.96, 131.79, 131.51, 130.95, 130.34, 129.53, 129.28, 129.05, 128.12, 127.30, 125.83, 121.32, 22.54; MS (DCI) m/e: 382 (MH$^+$); IR (KBr): 3438, 1686, 1594, 1518.
Anal. calcd. for $C_{25}H_{19}O_3N_1$: C, 78.72; H, 5.02; N, 3.67. Found: C, 78.35; H, 4.70; N, 3.47.
4-[[[8-(2-Methylphenyl)-2-naphthalenyl]]carbonyl]amino]benzoic acid ($I^2$e) ($^{R7}$=CH$_3$; $R^8, R^9, R^{10}$=hydrogen)
Yield: 52%; $^1$H-NMR: δ12.79 (bs, 1H), 10.62 (bs, 1H), 8.17 (d, J=8.6 Hz, 1H), 8.09 (m, 2H), 7.92 (m, 5H), 7.72 (m, 1H), 7.41 (m, 4H), 7.26 (d, J=7.1 Hz, 1H), 1.97 (s, 3H); $^{13}$C-NMR: 168.65, 167.70, 144.92, 142.00, 140.74, 137.68, 136.33, 134.05, 132.30, 132.01, 131.92, 131.84, 130.28, 129.71, 129.41, 129.25, 129.13, 128.21, 127.60, 127.31, 125.73, 121.36, 121.23, 21.54; MS (DCI) m/e: 382 (MH$^+$); IR (KBr): 3432, 1686, 1594, 1520.
Anal. calcd. for $C_{25}H_{19}O_3N_1$.0.25 $H_2O$: C, 77.81; H, 5.09; N, 3.63. Found: C, 78.12; H, 5.06; N, 3.58.
4-[[[8-(3,4-Dimethylphenyl)-2-naphthalenyl]carbonyl] amino]benzoic acid ($I^2$f) ($R^7, R^8$=hydrogen; $R^9, R^{10}$=CH$_3$)
Yield: 50%; $^1$H-NMR: δ12.78 (bs, 1H), 10.65 (s, 1H), 8.46 (s, 1H), 8.16 (d, J=8.6 Hz, 1H), 8.05 (m, 1H), 7.93 (m, 5H), 7.69 (m, 1H), 7.50 (d, J=6.3 Hz, 1H), 7.28 (m, 3H), 2.32 (s, 6H); $^{13}$C-NMR: 168.66, 167.99, 144.99, 142.64, 138.71, 138.25, 137.48, 136.60, 134.02, 132.62, 131.96, 131.84, 131.34, 130.31, 129.45, 129.25, 129.01, 128.95, 128.23, 127.28, 125.78, 121.29, 21.18, 20.87; MS (DCI) m/e: 396 (MH$^+$); IR (KBr): 3050, 1688, 1520, 1406.
Anal. calcd. for $C_{26}H_{21}O_3N_1$.0.25 $H_2O$: C, 78.08; H, 5.42; N, 3.50. Found: C, 78.13; H, 5.24; N, 3.38.
4-[[[8-(2,4 -Dimethylphenyl)-2-naphthalenyl]carbonyl] amino]benzoic acid ($I^2$g) ($R^7, R^9$=CH$_3$; $R^8, R^{10}$=hydrogen)
Yield: 49%; $^1$H-NMR: δ12.77 (bs, 1H), 10.61 (s, 1H), 8.16 (d, J=8.6 Hz, 1H), 8.08 (m, 2H), 7.99 (s, 1H), 7.91 (m, 4H), 7.70 (m, 1H), 7.41 (d, J=6.7 Hz, 1H), 7.21 (s, 1H), 7.14 (s, 2H), 2.38 (s, 3H), 1.93 (s, 3H); $^{13}$C-NMR: 168.67, 167.77, 144.94, 142.08, 138.81, 137.83, 137.44, 136.34, 134.01, 132.50, 131.93, 131.85, 130.26, 129.52, 129.25, 128.99, 128.32, 128.21, 127.33, 125.67, 121.38, 22.53, 21.50; MS (DCI) m/e: 396 (MH$^+$); IR (KBr): 3432, 1686, 1594, 1518.
Anal. calcd. for $C_{26}H_{21}O_3N_1$: C, 78.97; H, 5.35; N, 3.54. Found: C, 78.81; H, 5.21; N, 3.38.
4-[[[8- 2-Isopropylphenyl)-2napthalenyl]carbonyl]amino] benzoic acid ($I^2$h) ($R^7$=—CH(CH$_3$)$_2$; $R^8, R^9, R^{10}$=hydrogen)
Yield: 27%; $^1$H-NMR: δ12.76 (bs, 1H), 10.59 (s, 1H), 8.17–7.96 (m, 4H), 7.88 (m, 4H), 7.69 (m, 1H), 7.47 (m, 3H), 7.33 (m, 1H), 7.17 (d, J=7.42 Hz, 1H), 2.48 (septet, J=6.70 Hz, 1H), 1.00 (t, J=6.45 Hz, 6H); MS (DCI) m/e: 410 (MH$^+$); IR (KBr): 2960, 1686, 1594, 1518.
Anal. calcd. for $C_{27}H_{23}O_3N_1$: C, 79.19; H, 5.66; N, 3.42. Found: C, 78.96; H, 5.73; N, 3.22.
4-[[[8-(2-Ethylphenyl) -2-naphthalenyl]carbonyl]amino] benzoic acid ($I^2$i) ($R^7$=—CH$_2$CH$_3$; $R^8, R^9, R^{10}$=hydrogen)

Yield: 50%; ¹H-NMR: δ12.77 (bs, 1H), 10.61 (s, 1H), 8.10 (m, 3H), 7.97 (s, 1H), 7.89 (m, 4H), 7.69 (m, 1H), 7.45 (m, 3H), 7.34 (m, 1H), 7.21 (d, J=7.4 Hz, 1H), 2.25 (m, 2H), 0.90 (t, J=7.5 Hz, 3H); ¹³C-NMR: 166.91, 165.91, 143.21, 142.09, 140.12, 138.41, 134.52, 132.21, 130.98, 130.34, 130.20, 128.48, 128.23, 127.82, 127.40, 126.70, 125.78, 125.56, 123.97. 119.64, 119.55, 25.87, 15.38; MS (DCI) m/e: 396 (MH⁺); IR (KBr): 1685, 1596, 1518, 1406.

Anal. calcd. for $C_{26}H_{21}O_3N_1 \cdot 0.67 H_2O$: C, 76.62; H, 5.52; N, 3.44. Found: C, 76.62; H, 5.35; N, 3.26

4-[[[8-(2-Fluorophenyl)-2-naphthalenyl]carbonyl]amino]benzoic acid (I²j) (R⁷=F; R⁸, R⁹, R¹⁰=hydrogen)

Yield: 68%; ¹H-NMR: δ12.77 (bs, 1H), 10.65 (s, 1H), 8.08–8.19 (m, 4H), 7.86–7.96 (m, 4H), 7.73 (m, 1H), 7.49–7.58 (m, 3H), 7.40 (m, 2H); MS(DCI) m/e: 386 (MH⁺); IR (KBr): 1686, 1518, 1504, 1406.

Anal. calcd. for $C_{24}H_{16}O_3N_1F_1$: C, 74.79; H, 4.19; N, 3.63. Found: C, 74.60; H, 4.59; N, 3.26.

4-[[[8-(2-Methoxyphenyl)-2-naphthalenyl]carbonyl]amino]benzoic acid (I²k) (R⁷=—OCH₃; R⁸, R⁹, R¹⁰=hydrogen)

Yield: 76%; ¹H-NMR: δ12.76 (bs, 1H), 10.60 (s, 1H), 8.08 (m, 2H), 8.02 (d, J=8.1 Hz, 1H), 7.89 (m, 4H), 7.67 (m, 1H), 7.48 (m, 2H), 7.27 (dd, J=7.4 Hz, 1.7 Hz, 1H), 7.20 (d, J=7.6 Hz, 1H), 7.11 (dt, J=7.4 Hz, 0.95 Hz, 1H), 3.63 (s, 3H); ¹³C-NMR: 166.90, 166.07, 156.74, 143.28, 137.93, 134.51, 131.87, 131.50, 130.79, 130.21, 129.61, 128.28, 128.06, 127.49, 127.33, 127.16, 125.49, 123.79, 120.65, 119.60, 119.51, 111.63, 55.35; MS (DCI) m/e: 398 (MH⁺); IR (KBr): 1684, 1594, 1518, 1406.

Anal. calcd. for $C_{25}H_{19}N_1O_4 \cdot 0.3H_2O$: C, 74.50; H, 4.90; N, 3.48. Found: C, 74.64; H, 4.90; N, 3.32.

EXAMPLE 9

4-[[[8-(4-Methoxycarbonylphenyl)2-naphthalenyl]carbonyl]amino]benzoic acid, methyl ester (I³a)

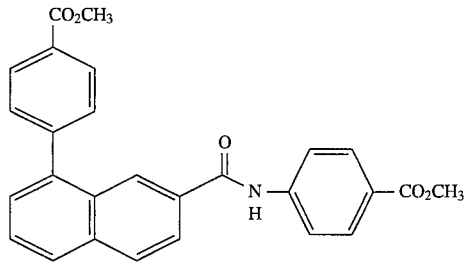

To a solution of 4-[[[8-bromo-2-naphthalenyl]carbonyl]amino]benzoic acid, methyl ester (Xb) (0.450 g, 1.17 mmoles) and p-tributyltin methylbenzoate (0.748 g, 1.76 mmoles) in dimethylformamide (5.00 mL) was added bis-(triphenylphosphine) palladium (II) chloride (0.125 g, 0.176 mmoles) and lithium chloride (0.149 g, 3.51 mmoles). The mixture was then stirred at 135° C. for 1 hour. The mixture was cooled to room temperature. Ethyl ether (3 mL) and saturated KF solution (5 mL) were added. After one hour, ethyl acetate (100 mL) and H₂O (100 mL) were added. The organic phase was evaporated and the residue was chromatographed on silica gel (eluted with 30% ethyl acetate in hexane) to give 60 mg (yield: 12%) of the title compound.

¹H-NMR (CDCl₃): δ8.40 (s, 1H), 8.22 (d, J=8.0 Hz, 2H), 8.03 (d, J=8.0 Hz, 2H), 7.98 (m, 4H), 7.50–7.78 (m, 6H), 4.00 (s, 3H), 3.95 (s, 3H).

MS(DCI) m/e: 440 ((MH⁺).

EXAMPLE 10

4-[[[8-(4-Carboxyphenyl)-2-naphthalenyl]carbonyl]amino benzoic acid (I⁴a)

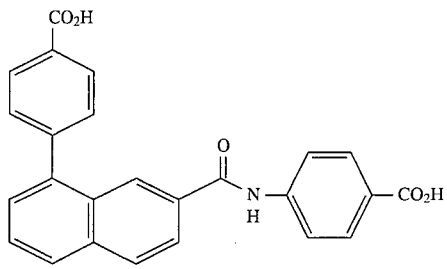

To a solution of 4-[[[8-(4-methoxycarbonylphenyl)-2-naphthalenyl]carbonyl]amino]benzoic acid, methyl ester (I³a) (60 mg, 0.14 mmol) in a 1:1 tetrahydrofuran and ethanol mixture (7 mL) was added 10N NaOH solution (0.20 mL, 2.0 mmol ) at room temperature. After 72 hours, the mixture was diluted with an excess of 1N HCl (50 mL). The precipitate was collected, washed with water and air dried to give 56 mg (yield: 82%) of the title product; ¹H-NMR: δ10.66 (s, 1H), 8.39 (s, 1H), 8.18 (d, J=8.6 Hz, 1H) 8.10 (m, 4H), 7.90 (m, 4H), 7.69 (m, 3H), 7.58 (dd, J=7.0 Hz, 0.9 Hz, 1H); ¹³C-NMR: 167.12, 166.90, 166.08, 143.92, 143.22, 139.70, 134.85, 132.60, 130.22, 130.01, 129.62, 128.77, 128.15, 127.55, 125.92, 125.56, 124.41, 119.62; MS(DCI) m/e: 412 (MH⁺); IR (KBr): 2992, 1690, 1608, 1522, 1408.

Anal. calcd. for: $C_{25}H_{17}O_5N_1 \cdot 1.5 H_2O$: C, 68.48; H, 4.59; N, 3.19. Found: C, 68.83; H, 4.38; N, 3.02.

Example 11

4-[[(8-Benzyl-2-naphthalenyl)carbonyl]amino ]benzoic acid, methyl ester (I⁵a)

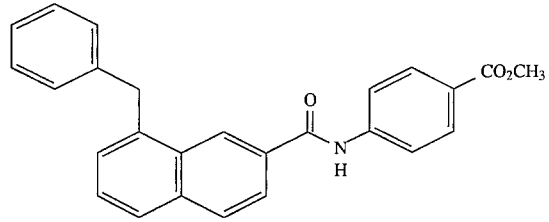

To a solution of phenylmagnesium chloride (2.0M solution in tetrahydrofuran, 3.12 mL, 6.31 mmol) in tetrahydrofuran (5 mL) at −78° C. was added a 1M zinc chloride solution in ether (6.31 mL, 6.31 mmol). After 1 hour at room temperature, [1,3-bis(diphenylphosphino)propane]nickel (II) chloride (74 mg, 0.13 mmol) and 4-[[[(8-bromo-2-naphthalenyl)carbonyl]amino]benzoic acid, methyl ester (Xb) (0.500 g, 1.31 mmol) were added and the mixture stirred at room temperature for 16 hours. The mixture was diluted with water (100 mL) and extracted with ethyl acetate (100 mL×2). The combined organic phase was evaporated and the residue was chromatographed on silica gel (eluted with 20% ethyl acetate in hexane) to give 0.317 g (yield: 61%) of the methyl ester as a tan solid.

¹H-NMR(CDCl₃): δ8.50 (s, 1H), 8.04 (d, J=8.0 Hz, 2H), 7.85 (m, 5H), 7.75 (d, J=8.0 Hz, 2H), 7.60 (m, 1H), 7.40–7.20 (m, 5H), 4.78 (s, 2H), 3.95 (s, 3H).

MS(DCI) m/e: 396 ((MH⁺).

EXAMPLE 12

4-[[(8-Benzyl-2-naphthalenyl)carbonyl]amino]benzoic acid (I⁶a)

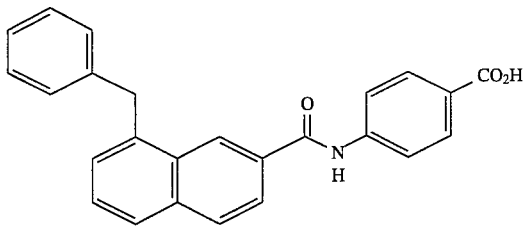

To a solution of 4-[[(8-benzyl-2-naphthalenyl) carbonyl] amino]benzoic acid, methyl ester (I⁵a) (317 rag, 0.802 mmoles) in ethanol (10 mL) was added a 10N NaOH solution (1.2 mL, 12 mmol) at room temperature. After 120 hours, the mixture was diluted with an excess of 1N HCl (100 mL). The precipitate was collected and air dried to give 239 mg (yield: 78%) of the title compound; ¹H-NMR: δ12.77 (bs, 1H), 10.67 (s, 1H), 8.73 (s, 1H), 8.04 (m, 2H), 7.94 (s, 4H), 7.89 (d, J=8.2 Hz, 1H), 7.57 (m, 1H), 7.41 (d, J=6.9 Hz, 1H), 7.23 (m, 5H), 4.54 (s, 2H); ¹³C-NMR: 167.00, 166.03, 143.36, 140.52, 138.55, 135.10, 131.83, 131.78, 130.74, 130.34, 128.93, 128.72, 128.57, 127.96, 127.79, 126.77, 126.18, 125.64, 124.82, 124.17, 119.75, 119.66, 37.85; MS (DCI) m/e: 382 (MH⁺); IR (KBr): 1682, 1648, 1520, 1406.

Anal. calcd. for $C_{25}H_{19}O_3N_1$: C, 77.19; H, 5.09, N, 3.63. Found: C, 77.42; H, 5.15; N, 3.44.

EXAMPLE 13

1-(8-Phenyl-2-naphthyl)ethanone (XIVa)

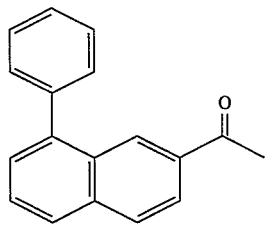

To a solution of 8-phenyl-2-naphthoic acid (0.795 g, 3.20 mmoles) in ethyl ether (15 mL) at −78° C. was added methyl lithium (1.4M solution in ethyl ether, 4.57 mL, 6.40 mmoles). The mixture was stirred at room temperature for 2 hours, washed with 1N HCl (100 mL), brine (100 mL), dried over anhydrous sodium sulfate and evaporated to give 0.550 g (yield: 70%) of the title compound; ¹H-NMR: δ8.53 (s, 1H), 8.05 (d, J=7Hz, 1H), 7.9 (m, 2H), 7.65 (m, 1H), 7.50 (m, 6H), 2.55 (s, 3H); MS (DCI) m/e: 247 (MH⁺).

EXAMPLE 14

4-[(E,Z)-2-(8-Phenyl-2-naphthalenyl)propenyl]benzoic acid, ethyl ester (I⁷a)

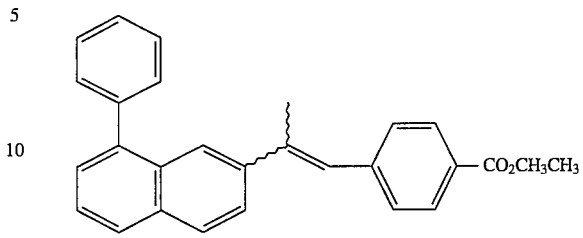

Methyl p-[(diethoxyphosphoryl)methyl]benzoate (4.00 g, 13.97 mmoles, prepared as in Liebigs Ann. Chem. 1985, 929) was added to a 1M dimsyl anion solution in dimethylsulfoxide (12.71 mL, 12.71 mmoles, prepared by warming sodium hydride in dimethylsulfoxide for 1 hour at 65° C.). After 30 minutes, the mixture was added to a solution of 1-(8-phenyl-2-naphthyl)ethanone (XIVa) (0.540 g, 2.19 mmoles) in dimethylsulfoxide (10.0 mL) at room temperature. After 2 hours at room temperature, a 1M solution of sodium ethoxide in ethanol (1.31 mL, 2.63 mmoles) was added. After 2 hours at room temperature, the mixture was diluted with saturated sodium bicarbonate (100 mL) and extracted with diethyl ether (100 mL×3). The solution was evaporated and the residue chromatographed (eluted with 5% ethyl acetate in hexane) over silica to give 0.500 g (yield: 64%) of 4-[2-(8-phenyl-2-naphthalenyl)-propenyl]benzoic acid, ethyl ester as a white solid. NMR indicated the ratio of E to Z isomers as 2:1.

EXAMPLE 15

4-[(E)-2(8-Phenyl-2-naphthalenyl)propenyl]benzoic acid (I⁸a)

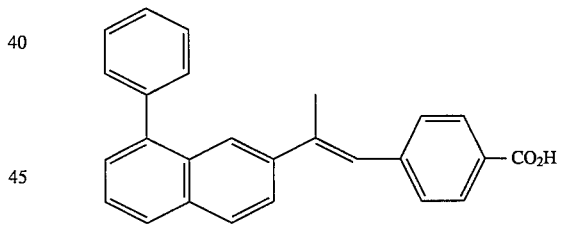

To a solution of 4-[2-(8-phenyl-2-naphthenyl)propenyl] benzoic acid, ethyl ester (2:1 mixture of E and Z isomers, 0.500 g, 1.28 mmoles) in ethanol (15 mL) was added a 10N NaOH solution (1.28 mL, 12.8 mmol) at room temperature. After 16 hours, the mixture was diluted with an excess of 1N HCl (100 mL) and then filtered. The solid was recrystallized from ethanol to provide the title compound (yield: 23%) as a white powder; ¹H-NMR: δ8.05 (d, J=8.7 Hz, 1H), 7.98 (m, 4H), 7.90 (d, J=8.7 Hz, 1H), 7.46–7.63 (m, 9H), 7.05 (s, 1H), 2.25 (s, 3H); IR (KBr): 3440, 1684, 1604.

Anal. calcd. for $C_{26}H_{20}O_2 \cdot 0.1H_2O$: C, 85.26; H, 5.56. Found: C, 85.19; H, 5.39.

The following biological test indicates that the compounds of the instant invention possess cytotoxicty activity normally associated with retinoids. Thus in one aspect, the invention provides a method of treating various tumors.

Cytotoxicity Result

The cytotoxicity assay was set up similar to those run by the National Cancer Institute (D. A. Scudiero, et al, "Evaluation of a Soluble Tetrazolium/Formazan Assay for Cell Growth and Drug Sensitivity in Culture Using Human and Other Tumor Cell Lines", *Cancer Research*, 48, 4827–4833, Sep. 1, 1988; M. C. Alley, et al, "Feasibility of Drug Screening with Panels of Human Tumor Cell Lines Using a Microculture Tetrazolium Assay", *Cancer Research*, 48, 589–601, Feb. 1, 1988) with the exception that the new vital stain alamarBLue™ was used to determine cellular viability. Briefly, the assayed involved plating 1000 cells per well in a volume of 120 µL in a 96 well flat-bottom dish (Corning) on day −1. Twenty-four hours later the appropriate dilution of a compound of formula I was added in a volume of 30 µL complete medium (final volume 150 µL). The plates were sealed with a plate sealer (Dynatech Labs) to prevent evaporation. On day 5 the mylar film was removed and 15 µL of sterile alamarBlue was added to each well and the cells were incubated 37° C. 5% $CO_2$ for two hours. Using a Vmax plate reader the optical density for each well was determined having the $OD_{570}$ subtracted from the $OD_{600}$. The 100% signal was determined for cells grown in complete medium containing only 0.5% DMSO. All wells were set-up in triplicate and the mean values were plotted in FIG. 1. The $IC_{50}$ values were determined for the second experiment and are listed in table 1.

TABLE 1

| $IC_{50}$ values for L2987 experiment 2 | |
| --- | --- |
| Compound | $IC_{50}$ (µM) |
| All trans retinoic acid | 68 |
| $I^2a$ | 72 |
| $I^2f$ | 49 |
| $I^2g$ | 54 |
| $I^2b$ | 39 |

The compounds of formula I may be used topically or systemically, as anticancer agents and in the treatment, amelioration, or prevention of the skin disorders and rheumatic illnesses for which retinoic acid and other retinoids are useful. In this regard, they may be used for therapy in animals, including humans, of premalignant epithelial cell lesions, as a prophylaxis against tumor promotion in epithelial cells and treatment for dermatoses such as ichthyoses, follicular disorders, benign epithelial disorders, and other proliferative skin diseases (nonnmalignant conditions of the skin that are characterized by epidermal cell proliferation or incomplete cell differentiation) such as acne, psoriasis, eczema, atopic dermatitis, nonspecific dermatitis and the like. The compounds of formula I may also be used in reversing and preventing the effects of irradiation damage to skin. When used for the above treatments they will usually be formulated with a pharmaceutically acceptable liquid, semi-solid, or solid carrier. A pharmaceutically acceptable carrier is a material that is nontoxic and generally inert and does not affect the functionality of the active ingredients adversely. Such materials are well known and include those materials sometimes referred to as diluents or vehicles (excipients) in the pharmaceutical formulation art. The carrier may be organic or inorganic in nature. Examples of pharmaceutically acceptable carriers that may be used to formulate a compound of formula I are water, gelatin, lactose, starch, mineral oil, cocoa butter, dextrose, sucrose, sorbitol, mannitol, gum acacia, alginates, cellulose, talc, magnesium stearate, polyoxyethylene sorbitan monolaurate, and other commonly used pharmaceutical carriers. In addition to a compound of formula I and carrier, the formulation may contain minor amounts of additives such as flavoring agents, coloring agents, thickening or gelling agents, emulsifiers, wetting agents, buffers, stabilizers, and preservatives such as antioxidants.

The dosages and dosage regimen in which the compounds of formula I are administered will vary according to the dosage form, mode of administration, the condition being treated and particulars of the patient being treated. Accordingly, optimal therapeutic concentrations will be best determined at the time and place through routine experimentation.

In the treatment of dermatoses, it will generally be preferred to administer the drug topically, though in certain cases such as treatment of severe cystic acne, oral administration may also be used. If the compounds according to the invention are used topically, it will be found that they exhibit a good activity over a very broad range of dilution; in particular, concentrations of the active compound or compounds ranging from 0.0005% to 2% by weight can generally be used. It is of course possible to use higher concentrations if this should become necessary for a particular application; however, the preferred concentration of active principle are from 0,002% to 1% by weight.

For topical administration the compounds of formula I are conveniently provided in the form of unguents, gels, creams, ointments, powders, dyeing compositions, solutions, suspensions, emulsions, lotions, sprays, adhesive plasters and impregnated pads. The compounds according to the invention can be mixed with inert nontoxic, generally liquid or pasty, bases suitable for topical treatment. Preparation of such topical formulations are well described in the art of pharmaceutical formulations as exemplified, for example, Remington's Pharmaceutical Science, Edition 17, Mack Publishing Company, Easton, Pa. Other medicaments can be added to such topical formulation for such secondary purposes as treating skin dryness, providing protection against light; other medications for treating dermatoses, preventing infection, reducing irritation, inflammation and the like.

The compounds according to the invention can also be used enterally. Orally, the compounds according to the invention are suitably administered at the rate of 2 µg to 2 mg per day per kg of body weight. The required dose can be administered in one or more portions. For oral administration, suitable forms are, for example, tablets, pills, dragees, syrups, suspensions, emulsions, solutions, powders and granules; a preferred method of administration consists in using pills containing from 0.1 mg to about 1 mg of active substance.

U.S. Pat. No. 4,876,381 issued on Oct. 24, 1989 to Lang et al. provides examples of formulations constituting gel, unguent, powder, cream, etc. for a retinoid compound. The aforesaid U.S. Patent can be used as a guide to formulate a compound of formula I and is herein incorporated by reference in its entirety.

Isotretinoin (Accutane®) and etretinate (Tegison®) are used clinically to treat severe recalcitrant cystic acne and severe recalcitrant psoriasis, including the erythrodermica and generalized pustular types, respectively. Their mode of use is amply illustrated in the Physician's Desk Reference, 47th Edition, 1993, published by Medical Economics Data. The compounds of formula I may also be used to treat severe recalcitrant cystic acne or severe recalcitrant psoriasis. In so doing, the compounds of the present invention may be used in a similar fashion to isotretinoin and etretinate; thus, the relevant sections on isotretinoin and etretinate in the Physician's Desk Reference will serve as a convenient guide which will obviate the need for any undue experimentation.

The compounds according to the invention can also be administered parenterally in the form of solutions or suspensions for intravenous or intramuscular perfusions or injections. In that case, the compounds according to the invention are generally administered at the rate of about 2 μg to 2 mg per day per kg of body weight; a preferred method of administration consists of using solutions or suspensions containing approximately from 0.01 mg to 1 mg of active substance per ml.

Several retinoids have been found to possess anti-tumor properties. Roberts, A. B. and Sporn, M. B. in "The Retinoids," Sporn M. B. Roberts, A. B. and Goodman, D. S., eds, 1984, 2 pp. 209–286, Academic Press, New York; Lippman, S. M., Kessler, J. F., and Meyskens, F. L., *Cancer Treat. Rep.*, 1987, 71, p. 391; ibid., p. 493. As used herein, the term "anti-tumor" includes both chemopreventative (prophylactic or tumor promotion inhibiting) and therapeutic (curative) use. For example, all-trans retinoic acid can be used to treat acute promyelocytic leukemia. Huang, M. et al., *Blood*, 1988, 72, p. 567. Isotretinoin has been shown to be useful in prevention of second primary tumors in squamous-cell carcinoma of the head and neck. Hong, W. K. et al., *N. Engl. J. Med.*, 1990, 323, p. 795.

The compounds of formula I can also be used in substantially the similar manner to retinoids for treating (both chemopreventively and therapeutically) various tumors. For the compounds of this invention, the anti-tumor dose to be administered, whether a single dose, multiple dose, or a daily dose, will of course vary with the particular compound employed because of the varying potency of the compound, the chosen route of administration, the size of the recipient, the type of tumor, and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. An oncologist skilled in the art of cancer treatment will be able to ascertain, without undue experimentation, appropriate protocols for the effective administration of the compounds of this present invention, such as by referring to the earlier published studies on retinoids found to have anti-tumor properties. For example, for the prevention of second primary tumors with a compound of formula I in squamous-cell carcinoma of the head and neck, an oncologist may refer to the study by Hong, W. K. et al. in *N. Engl. J. Med.*, 1990, 323, p. 795. For treating acute promyelocytic leukemia, s/he may refer to the study by Huang, M. et al. in *Blood*, 1988, 72, p. 567.

What is claimed is:

1. A compound of formula I

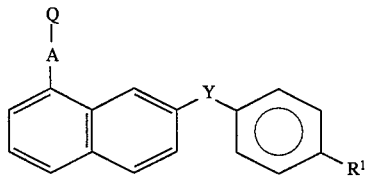

or a nontoxic pharmaceutically acceptable salt, physiologically hydrolyzable ester or solvate thereof, in which Y is —CO—NH—, —CR$^2$=CR$^3$—, —CO—O—, —O—CO—, —C(=S)—NH—, —C≡C—, —O—CH$_2$—, —CH$_2$—O—, or —CH$_2$—CH$_2$—;

A is —(CH$_2$)$_t$— or a bond;

Q is phenyl optionally substituted with one to three same or different C$_{1-6}$alkyl, C$_{1-6}$alkoxy, halogen, or —CO$_2$R$^4$;

R$^1$ is —CO$_2$Z, —CONHR$^5$, C$_{1-6}$alkyl, —CH$_2$OH, or —CHO;

R$^2$, R$^3$, R$^4$, R$^5$, and Z are independently hydrogen or C$_{1-6}$alkyl;

t is one to six; and with the proviso that —A—Q cannot be

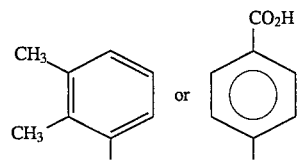

when Y is —CO—NH—.

2. A compound of claim 1 in which Y is —CO—NH—, A is a bond, and R$^1$ is COOH.

3. The compound of claim 2 that is 4-[[(8-phenyl-2-naphthalenyl)carbonyl]amino]benzoic acid.

4. The compound of claim 2 that is 4-[[[8-(3,5-dimethylphenyl)- 2-naphthalenyl]carbonyl]amino]benzoic acid.

5. The compound of claim 2 that is 4-[[[8-(3-methylphenyl)- 2-naphthalenyl]carbonyl]amino]benzoic acid.

6. The compound of claim 2 that is 4-[[[8-(4methylphenyl)- 2-naphthalenyl]carbonyl]amino]benzoic acid.

7. The compound of claim 2 that is 4-[[[8-(2-methylphenyl)- 2-naphthalenyl]carbonyl]amino]benzoic acid.

8. The compound of claim 2 that is 4-[[[8-(3,4-dimethylphenyl)- 2-naphthalenyl]carbonyl]amino]benzoic acid.

9. The compound of claim 2 that is 4-[[[8-(2,4-dimethylphenyl)- 2-naphthalenyl]carbonyl]amino]benzoic acid.

10. The compound of claim 2 that is 4-[[[8-(2-isopropylphenyl)- 2-naphthalenyl]carbonyl]amino]benzoic acid.

11. The compound of claim 2 that is 4-[[[8-(2-ethylphenyl)- 2-naphthalenyl]carbonyl]amino]benzoic acid.

12. The compound of claim 2 that is 4-[[[8-(2-fluorophenyl]- 2-naphthalenyl)carbonyl]amino]benzoic acid.

13. The compound of claim 2 that is 4-[[[8-(2-methoxyphenyl)- 2-naphthalenyl]carbonyl]amino]benzoic acid.

14. A compound of claim 1 in which Y is —CO—NH—, A is —CH$_2$—, and R$^1$ is COOH.

15. The compound of claim 14 that is 4-[[(8-benzyl-2-naphthalenyl)carbonyl]amino]benzoic acid.

16. A compound of claim 1 in which Y is —C(CH$_3$)=CH—, A is a bond, and R$^1$ is COOH.

17. The compound of claim 16 that is 4-[(E)-2-(8-phenyl-2-naphthalenyl)propenyl]benzoic acid.

18. A pharmaceutical formulation comprising any one of compounds as claimed in claims 1 to 17.

* * * * *